United States Patent [19]
Garbassi et al.

[11] Patent Number: 5,633,353
[45] Date of Patent: May 27, 1997

[54] HALOGENATED ORGANOMETALLIC COMPLEXES AND THEIR USE IN THE POLYMERIZATION OF UNSATURATED MONOMERS

[75] Inventors: Fabio Garbassi; Paolo Biagini, both of Novara; Piero Andreussi, Milan; Gabriele Lugli, S. Donato Milanese, all of Italy

[73] Assignee: Enichem Elastomeri S.r.l., Milan, Italy

[21] Appl. No.: 283,258

[22] Filed: Aug. 1, 1994

[30] Foreign Application Priority Data

Aug. 6, 1993 [IT] Italy ................. MI93A1794

[51] Int. Cl.$^6$ ................................ C07F 5/00
[52] U.S. Cl. ............................................. 534/15
[58] Field of Search .................................. 534/15

[56] References Cited

U.S. PATENT DOCUMENTS 4,668,773  5/1987  Marks et al. ............... 534/15
5,171,847 12/1992  Snaith et al. ............... 534/16

OTHER PUBLICATIONS

Fan et al., Journal of Organometallic Chem., vol. 376 (1989) pp. 61–66.
Fan et al., Journal of Organometallic., vol. 377 (1989) p. 51.

Primary Examiner—C. H. Kelly
Attorney, Agent, or Firm—Oblon, Spivak, McClelland, Maier & Neustadt, P.C.

[57] ABSTRACT

Organometallic complexes of lanthanides with a well-defined stoichiometry which can be used in the stereospecific polymerization of unsaturated monomers, can be represented by the general formula:

$$Me(Ar)(AlX_3R)_3 \qquad (1)$$

wherein: Me represents a metal with atomic number 21, 39, or an atomic number of between 57 and 71, Ar represents benzene or a susbstituted benzene with from 1 to 3 alkyl groups containing from 1 to 10 carbon atoms, X is a halogen atom, whereas R is a linear, cyclic or branched alkyl radical containing from 1 to 12 carbon atoms;

the preparation of the complexes is described together with their use in the stereospecific copolymerization of unsaturated monomers.

9 Claims, 2 Drawing Sheets

HALOGENATED ORGANOMETALLIC COMPLEXES AND THEIR USE IN THE POLYMERIZATION OF UNSATURATED MONOMERS

BACKGROUND OF THE INVENTION

1. Field of the Invention

The present invention relates to new organometallic complexes comprising elements belonging to the group of lanthanides, their preparation and their use in the stereospecific polymerization of unsaturated monomers.

A metal belonging to the group of lanthanides means, as generally accepted in the known art, a metal belonging to the group comprising: Scandium, having atomic number 21, Yttrium, having atomic number 39, and/or a metal having an atomic number of between that of Lanthanium (57) and Lutetium (71); these metals form part of group IIIA of the periodic table, according to the IUPAC definition prior to the year 1985.

2. Description of the Related Art

It is known in the art that the halides of lanthanides form a group of products used as precursors, both for the preparation of a large number of organometallic derivatives of lanthanides, and for the embodiment of particular catalytic processes, such as for example the polymerization of unsaturated monomers.

Their preparation is easy but their use is complicated by their complete insolubility in all hydrocarbons of any type, because they are characterized by polymeric-type structure, with halogen bridges and difficult to break.

A complete description of the crystalline and molecular structure of the halides of lanthanides can be found in the well-known treatise on structural inorganic chemistry edited by A. F. Wells "Structural Inorganic Chemistry" published by Clarendon Press, Oxford, 1975.

However, precisely because of this compact structure, when these halides are used as precursors in the synthesis of organometallic derivatives, it is necessary to resort to the use of basic-type reaction solvents, such as ethyl ether or tetrahydrofuran, which are capable of breaking their polymeric structure, making them more vulnerable to the chemical reagents with which they are to react.

This technique cannot be used however when the same halides are to be used in the preparation of catalytic systems, such as in the case of polymerization, in which the basic environment of the solvent is not compatible with the reagents in use and with the catalysis mechanism.

The known art describes an elegant method for breaking the above polymeric structure of lanthanide chlorides. This method consists in preparing complexes having the general formula:

$$Me(Ar)(AlCl_4)_3$$

wherein: Me represents a metal belonging to the group of lanthanides and Ar represents a substituted or non-substituted benzene group.

Valid preparative methods for derivatives wherein Me is lanthanium, neodymium, samarium and X is chlorine, are disclosed in articles appearing in the magazines: a) *Organometallics*, vol. 4, page 942 of 1985 and vol. 6 page 1275 of 1987; b) *Journal of Organometallic Chemistry*, vol. 376, page 51 of 1989 and vol. 377, page 61 of 1989.

The crystalline and molecular structure of the complexes indicated in the above articles, show the presence of monomeric units $MeCl_3$ complexed with 3 $AlCl_3$ groups and an aromatic hydrocarbon binder.

In spite of the fact that the complexes of the known art having the general formula $Me(Ar)(AlCl_4)_3$ quoted above, contain, as can be seen, the $MeCl_3$ groups in monomeric form, they still have the great disadvantage however of being completely insoluble in aliphatic hydrocarbons.

This characteristics considerably limits their use in all reactions, such as for example the polymerization of olefins and diolefins, in which the solubility of the catalyst precursor is greatly desired for its simplicity of use and reproducibility of the catalytic activity.

SUMMARY OF THE INVENTION

The purpose of the present invention is consequently the preparation of new organometallic complexes comprising elements belonging to the lanthanide family, which overcomes the drawbacks of the known art mentioned above and which, as well as being produced with a well-defined stoichiometry and not in polymeric form, are soluble in aliphatic, cyclo-aliphatic and aromatic organic solvents, generally used for polymerization reactions.

It has in fact been found by the applicant, and this forms a first aspect of the present invention, that if a complex having general formula $Me(Ar)(AlX_4)_3$, hereinafter referred to as "reagent A", is reacted, in a precise molar ratio, with an aluminium trialkyl with general formula $AlR_3$, hereinafter referred to as "reagent B", wherein R has the meaning defined above, a compound with a defined stoichiometry is obtained, hereinafter called "product (C)", whose structure can be represented with the general formula (1) $Me(Ar)(AlX_3R)_3$, wherein Me, Ar, R and X have the meaning defined above. These complexes are isolated as solid compounds with a well-defined stoichiometry, and are therefore univocally defined chemical compounds to all effects.

In accordance to what has been specified above and according to a second aspect, the present invention relates to organometallic complexes of lanthanides, which can be represented by the general formula, $$Me(Ar)(AlX_3R)_3 \qquad (I)$$

wherein:

Me represents a metal of the group IIIA, having atomic number 21, 39, or an atomic number of between 57 and 71, Ar represents benzene or a benzene substituted with from 1 to 3 alkyl groups containing from 1 to 10 carbon atoms, X is a halogen atom, whereas, R is a linear, cyclic or branched alkyl radical containing from 1 to 12 carbon atoms.

The present invention also relates, and this constitutes a further aspect of the present invention, to the synthesis method for the preparation of the same compounds as general formula (I) and to the use of these complexes in the polymerization of olefine and/or diolefine monomers.

The complexes belonging to general formual (I) above form a new chemical series, with a defined stoichiometry and can be characterized with modern spectroscopic research techniques as well as with the centesimal chemical analyses of the elements of which they consist.

A preferred aspect of the present invention relates to catalytic complexes of general formula (I), wherein Me is respectively an Yttrium atom (Y), a Neodymium (Nd) or a Praseodymium atom (Pt), Gadolinium atom (Gd) and Ytterbium atom (Yb).

Another preferred aspect of the present invention relates to catalytic complexes of general formula (I) wherein X is a chlorine or bromine atom.

An equally preferred aspect of the present invention relates to catalytic complexes of general formula (I) wherein Ar is toluene or 1,2,4,5-tetramethylbenzene (durene).

A further aspect of the present invention relates to catalytic complexes of general formula (I) wherein R represents a methyl, ethyl, n-butyl or isobutyl group respectively.

As mentioned above, the present invention also relates to the preparative method used for the synthesis and separation of the compounds. The reaction is carried out using the process selected by the applicant, i.e. by suspending the reagent (A) [Me(Ar)(AlX$_4$)$_3$] at room temperature (at this temperature (A) is practically insoluble) in an aromatic, aliphatic, cycloaliphatic hydrocarbon and adding a solution of the reagent (B) [AlR$_3$], dissolved in the same solvent, to the suspension. In this way the desired product (C) is formed, i.e. the compound of general formula (I), soluble in the reaction solvent, which is recovered as a crystalline solid after the solution has been concentrated and cooled.

Non-limiting examples of solvents which can be used are: benzene, toluene, hexane, cyclohexane and their mixtures. The choice of the most suitable solvent is determined by the nature of component (B) which determines the solubility characteristics of the final compound (C) in that it determines the nature of the R group of formula (1). For example, if (B) is AlMe$_3$ the products are very soluble in toluene and in the mixture toluene-hexane, but are scarsely soluble in hexane whereas if (B) is Al(C$_4$H$_9^i$)$_3$ the relative derivative (C) is also soluble in cyclohexane and in hexane.

The preparation of the crystalline complexes with a well-defined structure and with general formula (I), is not a simple and obvious consequence of what is already known in the art.

In fact, it has been found by the applicant that only by using a molar ratio of (B)/(A) of 1.5, i.e. 1.5 moles of (B) per mole of (A), is it possible to isolate products (C) with a defined stoichiometry from the reaction medium. The molar ratio between (A) and (B) has a determinant importance in obtaining product (C), and it was neither easy to guess or foresee from what is known in the art.

From an operating point of view, the solution of reagent (B) is added to the suspension of reagent (A) within 30–60 minutes under vigorous stirring and the reaction is continued until the solid has completely dissolved in the suspension, which generally occurs within 120 –180 minutes from the beginning of the reaction. The solution can then be evaporated from the solvent under forced vacuum ($10^{-2}$ Pa) to obtain a white or slightly coloured residue which can be purified by dissolution in a mixture of toluene-hexane and subsequent crystallization at a low temperature.

Operating under the best conditions, monocrystals can be obtained from the crystallization, which can be used, apart from for centesimal chemical analyses and obtaining infrared spectra therefrom, also for X-ray diffraction measurements to obtain the molecular and crystalline structure of the derivatives. If the reaction is carried out with higher (B)/(A) molar ratios, for example from 2 to 15, component (A) still dissolves but it is impossible to recover solids of defined composition from the solution. In addition, if complex (B) is Al trimethyl, and the reaction is carried out with a ratio higher than 6, during the addition of component (B), the dissolution of component (A) is first noted, followed by the precipitation of an abundant precipitate. The solid, separated and analyzed, always proves to be an undefined composition.

As a result of what is specified above, the present invention equally relates to a process for the preparation of organometallic complexes of lanthanides, which can be represented by the general formula,

$$Me(Ar)(AlX_3R)_3 \qquad (I)$$

wherein:
Me represents a metal of group IIIA, having atomic number 21, 39, or an atomic number of between 57 and 71,
Ar represents benzene or a benzene substituted with from 1 to 3 alkyl groups containing from 1 to 10 carbon atoms,
X is a halogen atom, whereas,
R is a linear, cyclic or branched alkyl radical containing from 1 to 12 carbon atoms, this process being characterized in that, the complex having general formula

$$Me(Ar)(AlX_4)_3 \qquad (II)$$

wherein Me, Ar and X have the same meaning specified above, is suspended at room temperature and in an aromatic or aliphatic or cyclo-aliphatic hydrocarbon solvent, and a solution, in the same solvent in which complex (II) is suspended, is added to the solution thus obtained, of the compound

$$AlR_3 \qquad (III)$$

wherein R has the same meaning defined above, and in such a quantity that the molar ratio (III)/(II)=1.5, and reacting at room temperature until the complete dissolution of the suspended solid (II):

The structure of the derivative obtained by the reaction of a mole of Nd(Toluene)(AlCl$_4$)$_3$ with 1.5 moles of Al (CH$_3$)$_3$ is shown in FIG. 1 at the foot of which are shown the most important crystallographic parameters. The structure represented should be considered general for all the complexes claimed in the present invention.

As specified above, the molar ratio (B)/(A) is critical for obtaining the compounds of the present invention. If this ratio is 1.5, using the procedure described, crystalline solids with a defined stoichiometry are recovered from the reaction solution. If this ratio exceeds the value of 1.5 the dissolution of derivative (A) still takes place but at the end of the operations derivatives with reproducible analyses and consequently with a defined structure are not isolated.

From the analysis of the structure shown in FIG. 1 it can be noted that the isolated compounds (C) are structurally very similar to the starting products (A) and can still be defined as halide complexes of lanthanides and aluminium with an aromatic hydrocarbon molecule linked to the central lanthanide atom.

Their most surprising characteristic is the high solubility when compared to the insolubility of the precursors (A).

This characteristic can be advantageously exploited in reactions which make use of lanthanide halides which, owing to their complete insolubility, must be used as solids in suspension.

It is also specified in the known art that the chlorides of lanthanides, of general formula LnCl$_3$ (Ln=Pr, Nd, Gd, etc), for catalytic systems for the polymerization of diolefins together with aluminium trialkyls of general formula AlR$_3$ wherein R maintains the meaning defined above.

The halides of lanthanides used can be halides with formula LnX$_3$ as such (Ln=lanthanide, X=Cl, BR, I) as indicated for example in the publication *Scientia Sinica*

(English edition), volume 13, page 1339 (1964). In this case however the relative catalysts have a limited activity in the polymerization of butadiene.

An improvement with respect to the known art has been obtained with the use of halides of lanthanides complexed with Lewis bases. In this respect, for example, patent CN 1057055 of 18 December 1991 and the article in *Macromolecules*, vol. 15, page 230 of 1982, describe the use in polymerization of complexes of $NdCl_3$ with tetrahydrofuran. The article appearing in *Scientia Sinica* (English edition) vol. 23, page 734 of 1980 and patent JP 83154705 of 14 September 1983, describe the use of lanthanide chlorides complexed with alcohols or alkyl-phosphates respectively, in the polymerization of butadiene.

Other bases suitable for complexing lanthanide halides are phosphoramides and pyridine oxide as claimed in patents JP 84113003 of 29 June 1984 and DD 243034 of 18 Febuary 1987 respectively. In all these cases the use of co-ordination compounds of lanthanide halides with Lewis bases produce active catalytic systems in the 1.4-cis polymerization of butadiene with an improved activity with respect to the use of halides alone.

Both systems based on halides or complexed halides however have two considerable drawbacks. First of all, they must be prepared with preformation techniques well-known to experts in the art, if a significant activity in polymerization is required. Secondly, both the starting halides and the preformed catalysts are completely insoluble in normal solvents used for polymerization and consequently all operations of preformation and charging into the polymerization reactor must be carried out in a heterogeneous phase.

This drawback makes it difficult the transfer and dosage of the suspension of the catalyst creating serious problems of reproducibility and dirtying of the industrial plant.

It has now been found by the applicant, and this forms a further aspect of the present invention, that the claimed complexes (C) can be advantageously used as soluble halides of lanthanides in the polymerization reaction of unsaturated monomers and in particular in the polymerization of high polymer butadiene with high degrees of 1.4-type chains (>99%).

In addition, by preparing the catalytic system from products in solution, it is not necessary to use preformation techniques to obtain high polymerization activities in short times. Finally, it has been found that the 1.4-type chains can vary from 1.4-cis to 1.4-trans by suitably modifying the nature of component (C) i.e. of the lanthanide atom in the complex.

The catalytic system based on the complexes claimed herein can be prepared by reacting the complex (C) selected with a hydride, alkyl or mixed compound of a metal belonging to groups IA, IIA and IIIA of the periodic table of elements (hereinafter referred to as compound (D) in a hydrocarbon solvent containing the monomer to be polymerized, using the operating procedure described below.

The desired quantity of monomer is dissolved in the polymerization solvent at 0° C. Compound (D) is then added in the selected ratio and, finally, compound (C) generally in the form of a solution in the same solvent used for the polymerization.

The solution of compound (C) can be made starting from the corresponding crystalline product, obtained described above and dissolved in the same solvent used for the polymerization. Or, this solution can also advantageously prepared by suspending the corresponding product (A) in the solvent used for the polymerization and reacting it with the suitable quantity of compound (B) until its complete dissolution in accordance with the procedure for the preparation of compounds (C). The solution obtained is used as such without the previous separation of the solid compound (C).

The molar ratio between compound (D) and compound (C) can vary from 100:1 to 3:1. This ratio preferably remains at between 6 and 25, the ratio 6 being preferred when (D) is $Mg(Bu)_2$ and 25 when (D) is $AlH(Bu^i)_2$.

The polymerization reaction is carried out at a temperature of between 0° and 70° C., preferably at 50° C, under stirring and can last for a few minutes to several hours depending on the catalytic system selected.

The reaction is blocked by introducing several $cm^3$ of methanol into the polymerization container under stirring and then pouring the whole contents of the container into an excess of methanol containing about 1% of a suitable antioxidant. The polymer, recovered as a solid insoluble in alcohol, is washed several times with methanol and dried with the mechanical vacuum pump. The dry elastomeric material is used for calculating the conversion and for physico-chemical analyses such as infrared analysis (IR), Gel Permeation Chromatography (GPC), differential calorimeter analysis (DSC) ect.

An interesting characteristic of the catalytic systems claimed in the present invention lies in the high activity shown in the polymerization of butadiene using catalytic systems prepared with the "in situ" technique well-known to experts in the field. Unlike the catalytic systems based on halides and modified halides of the known art, it is not necessary to preform the catalyst and make it age to have a significant activity in polymerization, as will be shown in the illustrative examples with parallel tests carried out with catalysts prepared "in situ" and "preformed".

As has already been pointed out in the known art of Ziegler-Natta polymerization, the nature of the alkylating compound often influences both the activity of the catalytic system and the molecular weight of the polymer obtained.

In our case, the activity is particularly high using compounds of the type $MgR_2$ as alkylating agent, with R having the meaning defined above. Among these the alkylating compound $Mg(Bu)_2$, which is available on the market also for industrial use, is preferred.

As will be shown in the illustrative examples, with this alkylating compound, it is possible to obtain catalytic systems in which the ratio moles of converted monomer/moles of lanthanide complex reaches the value of $10^6$ even operating on bench scale.

With respect to the molecular weight, polymers with particularly suitable Mw values are obtained when the compound $AlH(Bu^i)_2$ is used as alkylating product.

Another interesting characteristic of the catalytic systems claimed herein lies in the possibility of varying the geometric stereoisomerism of the polymer produced by passing from a prevalently 1.4-cis taxis of 97% to a prevalently 1.4-trans taxis. This can be achieved by varying the lanthanide atom used as catalyst.

Finally it is interesting to note how the catalytic systems claimed herein can polymerize different types of unsaturated monomers such as conjugated α-olefins and diolefins such as butadiene, isoprene, pentadiene etc.

Illustrative examples are given for the preparation of derivatives (A) using a modified method with respect to literature, examples of the preparation of compounds (C) and their use in the polymerization of unsaturated monomers in accordance with the procedure claimed by the applicant.

DESCRIPTION OF THE PREFERRED EMBODIMENT

These examples are illustrative and do not limit the present invention in any way. The alkylating compounds used for the experiments such as Al(Bu$^i$)$_3$, AlH(Bu$^i$)$_2$, Al(CH$_3$)$_3$, Mg(Bu)$_2$, Li-Butyl were purchased from Aldrich Italia and used as such or diluted.

Figure 2:
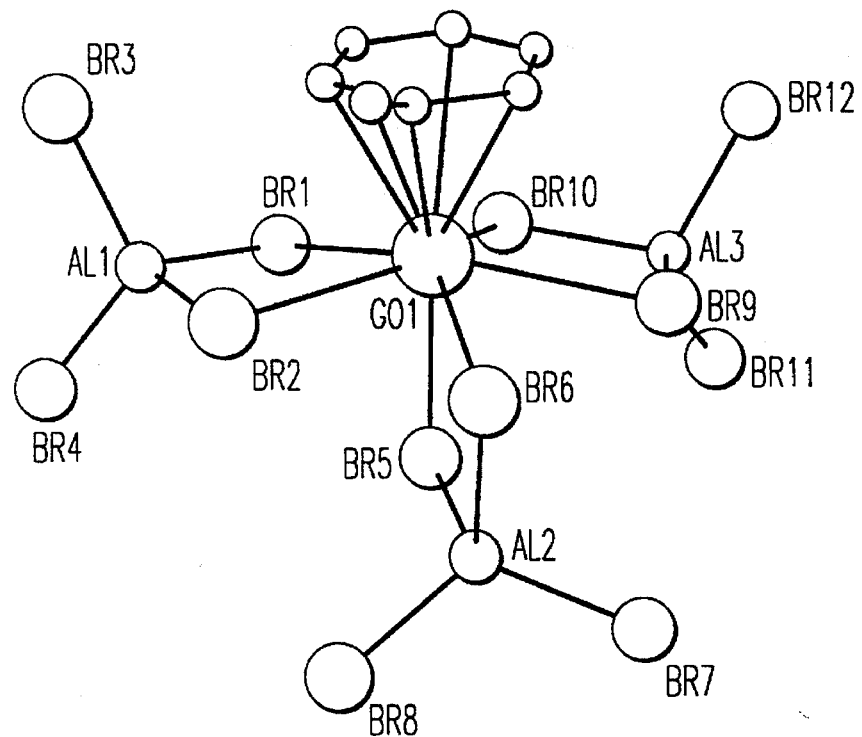
FIG. 2 shows the molecular and crystalline structure of Gd(tol)(AlBr$_4$)$_3$.
Figure 3:
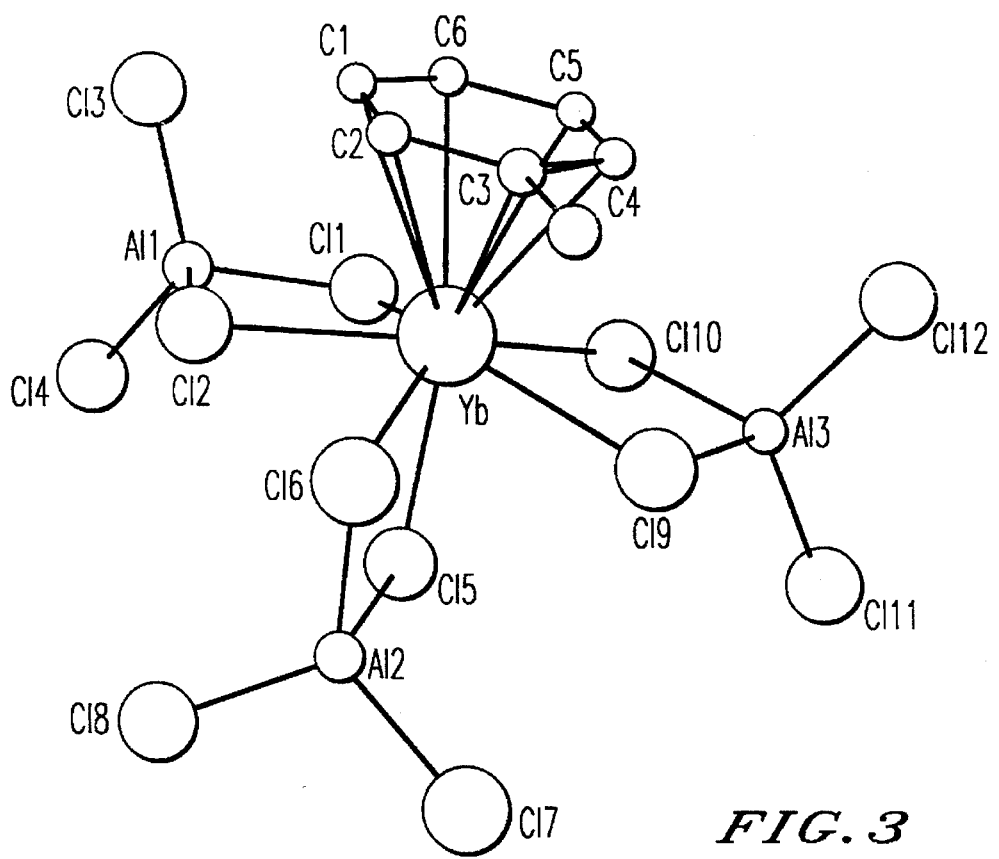
FIG. 3 shows the molecular and crystalline structure of Yb(tol)(AlCl$_4$)$_3$.

Table 1 shows the yields of final crystalline product and centesimal analyses. The structures obtained from monocrystals by X-ray diffraction (FIGS. 2 and 3) of the compounds obtained in examples 5 and 6 are indicated showing the complete structural identity between complexes prepared according to our method and the complexes known in literature.

TABLE 1

Preparation of the complexes of general formula Ln(tol)(AlX$_4$)$_3$

| Ex. N° | Compound$^a$ | Color | Yield$^b$ (%) | Analysis$^c$ Ln | Al(%) | Halogen(%) |
|---|---|---|---|---|---|---|
| 2 | Pr(tol)(AlCl$_4$)$_3$ | Green | 91 | 19.1(19.6) | 10.7(10.9) | 56.8(57.5) |
| 3 | Nd(tol)(AlBr$_4$)$_3$ | Light blue | 80 | 11.4(11.3) | 6.0(6.3) | 75.2(75.3) |
| 4 | Nd(tol)(AlI$_4$)$_3$ | Light blue | 69 | 8.3(7.8) | 4.4(4.4) | 82.1(82.8) |
| 5 | Gd(tol)(AlBr$_4$)$_3$ | No color | 83 | 12.4(12.2) | 5.9(6.3) | 73.9(74.4) |
| 6 | Yb(tol)(AlCl$_4$)$_3$ | Orange | 63 | 21.6(22.4) | 11.3(10.5) | 55.2(55.1) |
| 7 | Y(tol)(AlCl$_4$)$_3$ | No color | 45 | 12.4(12.9) | 12.7(11.8) | 61.6(61.9) |
| 8 | Sm(tol)(AlCl$_4$)$_3$ | Yellow | 78 | 19.7(20.1) | 10.9(10.8) | 56.1(56.8) |

$^a$Reactions carried out in toluene at boiling point
$^b$Calculated on starting product
$^c$The calculated values are shown in brackets.

EXAMPLE 1

Preparation of the Compound Nd(toluene)(AlCl$_4$)$_3$.

The process followed is a modification of the one described in the *Journal of Organometallic Chemistry*, vol. 376, page 51 of 1989. The main modification concerns the elimination of the aluminium powder which proves to be unnecessary for the synthesis and use of toluene as solvent.

The change of solvent only changes the aromatic molecule co-ordinated to the neodymium atom. In addition, we have extended the process, with success, to bromides and iodides of lanthanides for the preparation of the corresponding brominated and iodinated complexes. The use of these halogens has not been cited so far in literature for elements of the group of lanthanides.

All the reaction phases were carried out with the rigorous exclusion of oxygen and humidity following the well-known vacuum/nitrogen techniques.

0.015 moles of NdCl$_3$, 100 cm$_3$ of toluene, 0.045 moles of AlCl$_3$ are charged into a flask equipped with a magnetic stirrer, reflux cooler and tap for the entrance of nitrogen. The flask is then heated to the boiling point of the toluene on an oil bath for 3 hours. At the end the reaction mixture is filtered, under a nitrogen flow, on a heated filter and about 100 cm$_3$ of hexane are added to the final limpid solution which is then placed in a refrigerator at 5° C. After a period ranging from 12 to 36 hours crystals are formed on the walls of the container, which are separated by filtration, dried and analyzed.

Yield g 10.0 (90%). centesimal analyses (calculated values in brackets): Nd %=19.3 (19.4), Al %=10.8(10.9), Cl %=56.7 (57.3).

EXAMPLES 2–8

Preparation of the Complexes Ln(arene)(AlX$_4$)$_3$.

Following the procedure indicated in example 1 complexes similar to type (A) of Pr, Gd, Sm, Y, Yb were prepared with different halogens.

EXAMPLE 9

Preparation of the Complex Nd(toluene)(AlCl$_3$CH$_3$)$_3$.

All the operations are carried out under nitrogen with the rigorous exclusion of air and humidity. 100 cm$^3$ of toluene and 7.5×10$^{-3}$ moles of the compound prepared in example 1 are charged into a 250 cm$^3$, 3-necked flask equipped with a magnetic stirrer, drip-funnel and tap for the nitrogen flow. The product is insoluble and therefore remains in suspension in the toluene.

22.5 cm$^3$ of an 0.5 molar solution of Al(CH$_3$)$_3$ are placed in the separating funnel and are slowly added dropwise, over a period of 40 minutes, into the toluene suspension below. The suspended solid slowly passes into a solution.

The stirring is continued for a further 30 minutes and, at the end, the whole solid is dissolved. The lipid solution is evaporated under vacuum until a residue of 10 cm$^3$ is obtained. 30 cm$^3$ of hexane are added to form layers on the toluene solution and the flask is then put in a refrigerator at −20° C. for 24 hours.

Abundant crystals are formed, which are separated by filtration, washed with a small quantity of pentane at 0° C. and dried at the vacuum pump at room temperature.

Figure 1:
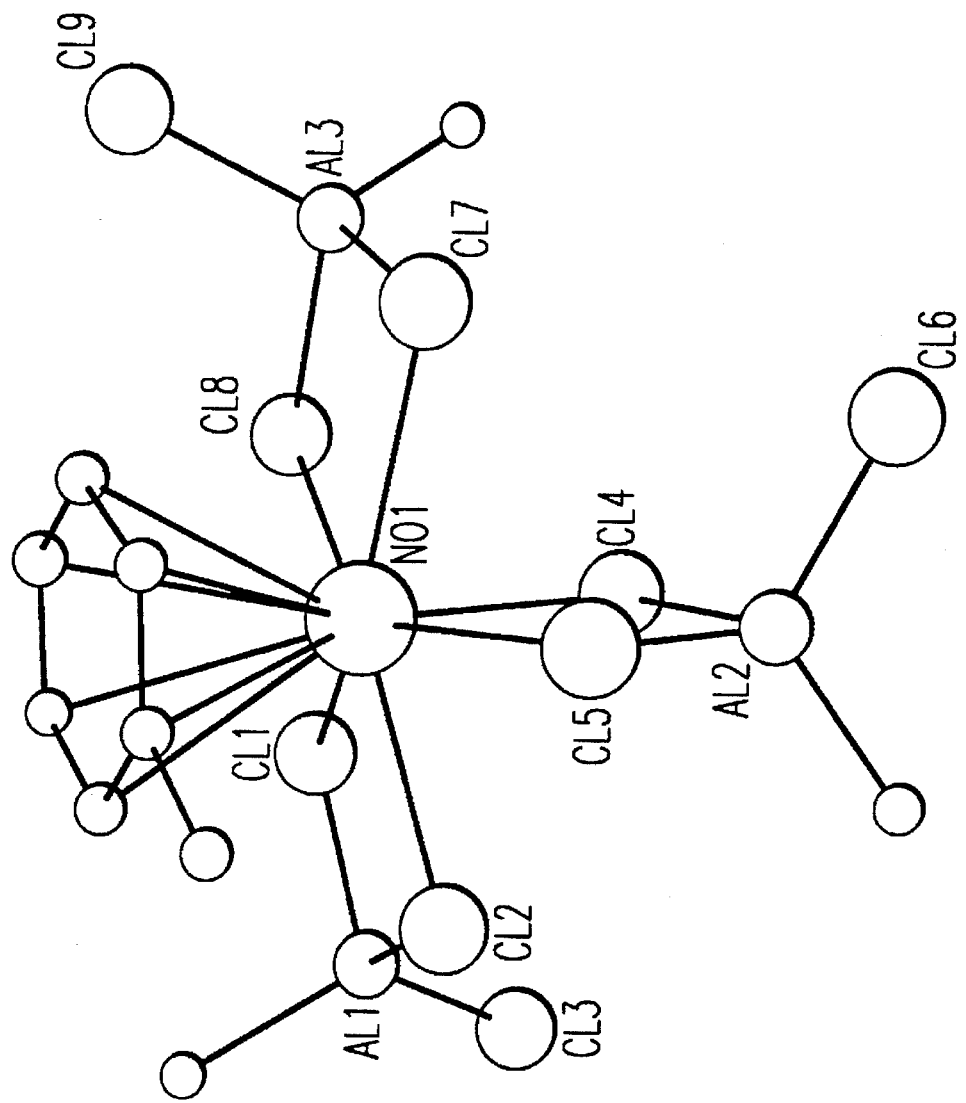
FIG. 1 shows the molecular and crystalline structure of $Nd(tol)(AlCl_3CH_3)_3$.

3.68 g of a pale blue crystalline solid are recovered. Analyses: Nd %=20.8; Al %=11.6; Cl %=46.5; the calculated values for Nd(toluene)(AlCl$_3$CH$_3$)$_3$ are: Nd %=21.2; Al %=11.9; Cl %=46.9. It was possible to obtain the crystalline and molecular structure of the compound by X-ray diffraction, which is shown in FIG. 1. EXAMPLES 10–15

Operating as described in example 8, type (C) complexes of different lanthanides and aluminium trialkyls are prepared. The examples show that the reaction for the preparation of complexes (C) is a general reaction for the type of lanthanide, type of aluminium, halogen and arene. The complexes prepared, the experimental conditions and final analyses are shown in Table 2

TABLE 2

Preparation of complexes having general formula $Ln(tol)(AlCl_3R)_3$ [a]

| Ex. N° | Initial Complex (A) | $AlR_3$ (B) | Final Complex (C) | Yield[b] (%) | Analysis[c] Ln | Al(%) | $CH_3$(%) |
|---|---|---|---|---|---|---|---|
| 10 | $Nd(tol)(AlCl_4)_3$ | $Al(C_2H_5)_3$ | $Nd(tol)(AlCl_3C_2H_5)_3$ | 66 | 19.0(19.9) | 11.5(11.2) | 43.0(44.1) |
| 11 | $Nd(tol)(AlBr_4)_3$ | " | $Nd(tol)(AlBr_3C_2H_5)_3$ | 76 | 11.8(12.8) | 7.5(7.2) | 65.2(64.0) |
| 12 | $Nd(tol)(AlI_4)_3$ | " | $Nd(tol)(AlI_3C_2H_5)_3$ | 72 | 9.1(9.3) | 5.1(5.2) | 74.4(73.9) |
| 13 | $Nd(dur)(AlCl_4)_3$[d] | " | $Nd(dur)(AlCl_3C_2H_5)_3$ | 69 | 18.5(18.8) | 10.7(10.6) | 42.2(41.7) |
| 14 | $Pr(tol)(AlCl_4)_3$ | " | $Pr(tol)(AlCl_3C_2H_5)_3$ | 66 | 19.2(19.6) | 11.9(11.2) | 43.9(44.3) |
| 15 | $Y(tol)(AlCl_4)_3$ | $Al(CH_3)_3$ | $Y(tol)(AlCl_3CH_3)_3$ | 58 | 13.2(14.2) | 11.9(12.9) | 52.6(50.9) |

[a]Reactions in toluene at 25° C. with $AlR_3/Ln = 1.5$ in moles;
[b]Calculated on the crystalline product obtained;
[c]Calculated values in brackets;
[d]dur = 1,2,4,5-tetramethylbenzene;

EXAMPLE 16

Preparation of the Solution of Component (C)

(Procedure 1)

$2.1 \times 10^{-3}$ moles of $Nd(Toluene)(AlCl_3C_2H_5)_3$ prepared from $Nd(toluene)(AlCl_4)_3$ and $Al(C_2H_5)_3$ according to the procedure described in example 9, are charged in an inert atmosphere into a large test-tube equipped with a lateral tap for the nitrogen flow and magnetic stirrer.

80 cm³ of toluene are then added and the mixture is left under stirring until the solid has completely dissolved. The solution obtained, which contains $0.26 \times 10^{-3}$ moles/litre of neodymium complex, is used for polymerization tests.

(Procedure 2)

$2.5 \times 10^{-3}$ moles of complex $Nd(toluene)(AlCl_4)_3$, 90 cm³ of hexane and $3.75 \times 10^{-3}$ moles of $Al(Bu^i)_3$ are charged in an inert atmosphere into a large test-tube equipped with a lateral tap for the nitrogen flow and magnetic stirrer. The mixture is left under stirring until the solid has completely dissolved. The resulting hexanoic solution, which contains $0.028 \times 10^{-3}$ moles/cm³ of neodymium complex, is directly used for polymerization tests.

EXAMPLE 17

Polymerization of Butadiene with the Complex $Nd(toluene)(AlCl_3C_2H_5)_3$ and $AlH(Bu^i)_2$.

A 200 cm³ drinking bottle, equipped with a magnetic stirrer and previously heated to 140° C., is cooled to room temperature under a perfectly dry nitrogen flow, to eliminate the air and environmental humidity. Maintaining the bottle under a nitrogen atmosphere and immersed in a bath at 0° C., the following are charged: 120 cm³ of anhydrous hexane, 20 g of anhydrous butadiene, the liquid having been removed from a small overturned cylinder with a hypodermic needle soldered to the cylinder valve, $3.7 \times 10^{-3}$ moles of $AlH(Bu^i)_2$ and 5.8 cm³ ($0.15 \times 10^{-3}$ moles) of a toluenic solution of the complex $Nd(toluene)(AlCl_3C_2H_5)_3$ of example 16, Procedure 1.

The bottle is then closed with a crown top equipped with a teflon seal, placed in a bath at 50° C., and magnetically stirred for 2 hours. The bottle is then rapidly cooled in a bath to 0° C., opened and the contents coagulated with about 300 cm³ of methanol containing 0.5 g of a suitable antioxidant. The coagulated polymer is collected, washed three times with methanol and then dried in a vacuum oven heated to 60° C. obtaining 16 g (conv. 80%) of dry polymer whose structure, upon IR analysis proves to be 98.1% of 1,4-cis, 1.6% of 1,4-trans and 0.3% of 1,2 structure.

EXAMPLE 18

Polymerization of Butadiene with Nd $(Toluene)(AlCl_3C_4H_9^i)_3$ and $Mg(Bu)_2$.

Following the operating procedure of the polymerization of example 17, 120 cm³ of hexane and 16 g of butadiene are charged into a bottle. The following are then added in order: 1.8 cm³ of the solution of example 16, Procedure 2, equal to $0.05 \times 10^{-3}$ moles of complex $Nd(Toluene)(AlCl_3Bu^i)_3$ and $0.3 \times 10^{-3}$ moles of $Mg(Bu)_2$ in a hexane solution. Polymerization is carried out at 50° C. for 15 minutes and 11.7 g of dry polymer (conv. 73%) are obtained, which upon IR analysis proves to have the structure 97.4% 1,4-cis, 1.8% 1,4-trans, 0.8% 1,2.

EXAMPLE 19

Polymerization of Butadiene with $Pr(Toluene)(AlCl_3C_4H_9^i)_3$ and Li (Butyl).

Following the operating procedure of the polymerization of example 17, 120 cm³ of anhydrous hexane and 16 g of butadiene are charged into a bottle. The following are then added in order: 2.3 cm³ ($0.25 \times 10^{-3}$ gAtoms of Pr) of a 0.11 molar solution of $Pr(toluene)(AlCl_3C_4H_9^i)_3$ prepared from $Pr(toluene)(AlCl_4)_3$ and $Al(Bu^i)_3$ according to the procedure of example 16, Procedure 2, and $2.5 \times 10^{-3}$ moles of a hexane solution of LiBu.

Polymerization is carried out at 70° C. for 2 hours and 7.6 g of dry polymer (54% conversion) are recovered.

EXAMPLES 20-29

High Polymer Butadiene with 1,4 Chains is Polymerized using the Catalytic Systems Obtained from the various Complexes $Ln(Arene)(AlX_3R)_3$ Prepared According to Procedures 1 or 2 of Example 16, Together with $AlH(Bu^i)_2$ or $Mg(Bu)_2$.

All the operations were carried out as in example 17. The polymerization conditions, conversions and IR analyses of the polymers are shown in table 3.

TABLE 3

Butadiene polymerization with Ln(toluene) (AlX$_3$C$_4$H$_9$)$_3$ [a]

| Ex. N° | Ln | X | AlR$_3$ [b] | Time min. | Convers. % | IR Analysis 1,4cis | 1,4trans | 1,2 | Mw ×10$^3$ |
|---|---|---|---|---|---|---|---|---|---|
| 20 | Pr | I | DIBAH | 60 | 46 | 98.8 | 1.0 | 0.2 | |
| 21 | Nd | Br | " | 120 | 34 | 98.8 | 1.1 | 0.1 | |
| 22 | Pr | Cl | " | 180 | 73 | | | | |
| 23[c] | Pr | Cl | DBM | 20 | 92 | 94.2 | 4.2 | 1.6 | 440 |
| 24[d] | Pr | Cl | " | 60 | 69 | | | | 1124 |
| 25 | Pr | I | " | 30 | 94 | 88.2 | 10.8 | 1.0 | 408 |
| 26 | Y | Cl | " | 20 | 87 | | | | |
| 27[c] | Nd | Br | " | 120 | 94 | 96.1 | 3.2 | 0.7 | |
| 28[e] | Gd | Cl | " | 15 | 70 | | | | |
| 29[e] | Nd | Cl | " | 15 | 53 | 97.6 | 1.8 | 0.6 | 994 |

[a] Solvent hexane; butadiene 15 g; Ln =0.05 × 10$^3$ gatoins; Temperature 50° C.
[b] DIBAH = diisobutylaluminiumhydrate, BIBAH/LN = 50; DBM = dibutylmagnesium; DBM/LN = 6;
[c] Solvent toluene; [d] 0° C.; [e] Ln = 0.02 × 10$^{-3}$ gAtoms;

EXAMPLE 30

High polymer butadiene with 1,4-cis chains is polymerized with a catalytic system obtained from Pr(toluene) (AlCl$_3$Bu$^i$)$_3$ and AlH(Bu$^i$)$_2$. The comparative polymerization tests show that the activity of the catalyst is not advantageously influenced by preformation techniques.
Preparation of the Preformed Catalyst (Procedure 3).

55 cm$^3$ of a 0.016×10$^{-3}$ molar hexane solution of Pr(toluene)(AlCl$_3$C$_4$H$_9^i$)$_3$, obtained by reaction of Pr (Toluene)(AlCl$_4$)$_3$ with the necessary quantity of Al(Bu$^i$)$_3$, are prepared in a 150 cm$^3$ graded test-tube equipped with a lateral tap for the nitrogen flow and magnetic anchor for the stirring, following the procedure described in example 16 procedure 2. 13.2×10$^{-3}$ moles (3.4 cm$^3$) of Al(Bu$^i$)$_3$ are added, under stirring, to this solution obtaining 57 cm$^3$ of a limpid solution which contains 0.015×10$^{-3}$ gAToms of Pr per cm$^3$ with a ratio Al/Pr equal to 15.
Polymerization with Preformed Catalyst.

Following the operating polymerization procedure of example 17, 120 cm$^3$ of hexane and 16 g of butadiene are charged into a bottle. 3.4 cm$^3$ (0.05×10$^{-3}$ gAtoms of Pr) of the solution of preformed catalyst prepared in Procedure 3 are then added, removing it immediately after the end of the addition of aluminium trialkyl. 1.75×10$^{-3}$ moles of AlH (Bu$^i$)$_2$ are then added. The polymerization is carried out at 50° C. for 3 hours obtaining 7.2 g of polymer (45% conversion) with a structure 95.6% 1,4-cis, 2.6% 1,4-trans, 1.8% 1,2.
Polymerization with Preformed and Aged Catalyst Operating as described in example 17, 120 cm$^3$ of anhydrous hexane, 18 g of butadiene and 3.4 cm$^3$ (0.05×10$^{-3}$ gAtoms of Pr) of the preformed catalyst solution, prepared in process 3, are charged into a bottle, removing them after the solution has been left under stirring, at room temperature, for 24 hours. 1.75×10$^{-3}$ moles of AlH(Bu$^i$)$_2$ are then added. The polymerization is carried out at 50° C. for 3 hours and 5.0 g (28% conversion) of polymer are obtained whose structure, upon IR analysis, proves to be 98.0% 1,4-cis, 1.2% 1,4-trans, 0.8% 1,2.
Comparative Polymerization with Catalyst Formed "In Situ".

Operating as described in example 17, 120 cm$^3$ of anhydrous hexane and 16 g of butadiene are charged into a bottle. 2.5×10$^{-3}$ moles of AlH(Bu$^i$)$_2$ in a hexane solution, and 0.05×10$^{-3}$ moles of Pr(toluene) AlCl$_3$Bu$^i$)$_3$ in a hexane solution, prepared from Pr(Toluene)(AlCl$_4$)$_3$, as described in example 16, process 2, are then added.

Polymerization is carried out at 50° C. for 3 hours obtaining 11.2 g of polymer (70% conversion) with a structure 97.8% 1,4-cis, 0.8% 1,4-trans, 1.4% 1,2.

EXAMPLE 31

High polymer butadiene with 1,4-cis chains is polymerized with a catalytic system obtained from Pr(toluene) (AlCl$_3$Bu$^i$)$_3$, Al(Bu$^i$)$_3$ and Mg(Bu)$_2$. The comparative polymerization tests show that the activity of the catalyst is not advantageously influenced by preformation and aging techniques.

Preparation of the Preformed Catalyst 43 cm$^3$ of a 0.021× 10$^{-3}$ hexane solution of Pr(toluene) (AlCl$_3$Bu$^i$)$_3$ and with a ratio Al/Pr of 15 obtained exactly with the procedure of Process 3 of example 30, are prepared in a 150 cm$^3$ graded test-tube, equipped with a later tap for the nitrogen flow and magnetic anchor for the stirring.
Polymerization with Preformed Catalyst Following the operating polymerization procedure of example 17, 120 cm$^3$ of hexane and 16 g of butadiene are charged into a bottle. 1.0 cm$^3$ (0.021×10$^{-3}$ moles of Pr) of the solution of preformed catalyst described above and 0.12×10$^{-3}$ moles of Mg(Bu)$_2$ in a hexane solution are then added. The bottle is polymerized at 50° C. for 20 minutes obtaining 12.8 g of polymer (80% conversion) with a structure 96.3% 1,4-cis, 2.7% 1,4-trans, 0.9% 1,2.
Polymerization with Preformed and Aged Catalyst Operating as indicated in example 17, 120 cm$^3$ of anhydrous hexane, 14 g of butadiene and 1.0 cm$^3$ (0.021×10$^{-3}$ gAtoms of Pr) of a solution of the preformed catalyst described above, after this has been left to age, under stirring, at room temperature for 24 hours, are charged into a bottle. 0.12×10$^{-3}$ moles of commercial Mg(Bu)$_2$ in a hexane solution are then added.

The polymerization is carried out at 50° C. for 20 minutes and 10.9 g (78% conversion) of polymer are obtained whose structure, upon IR analysis, proves to be 98.0% 1,4-cis, 1.2% 1,4-trans, 0.8% 1,2.
Comparative Polymerization with Catalyst Prepared "In situ"

Using the procedure indicated in example 17, 120 cm$^3$ of anhydrous hexane, 16 g of butadiene, 0.02×10$^{-3}$ moles of Pr(toluene)(AlCl$_3$Bu$^i$)$_3$ in a hexane solution prepared according to example 16, Procedure 2 and 0.12×10$^{-3}$ moles of commercial Mg(Bu)$_2$ hexane solution are charged into a bottle. The polymerization is carried out at 50° C. for 20 minutes obtaining 14.7 g (92% conversion) of polymer which, upon IR analysis, proves to have the following structure: 96.9% 1,4-cis, 2.0% 1,4-trans, 1.1% 1,2.

EXAMPLE 32

The polymerization of ethylene using a catalyst consisting of Nd(toluene)(AlCl$_3$CH$_3$)$_3$ and Mg(Bu)$_2$ is illustrated.

The air and environmental humidity is accurately eliminated using the known vacuum/nitrogen technique from an autoclave, equipped with a turbine stirrer, thermoresistance for reading the internal temperature, two valves for the input of the liquids and spherical valves for discharging to the bottom.

The following are then charged, under an inert atmosphere and in order: 200 cm$^3$ of anhydrous hexane, 12 cm$^3$ of a 0.0125 molar toluene solution of Nd(toluene)-(AlCl$_3$C$_4$H$_9$)$_3$ prepared according to the procedure of example 16, Procedure 1, 10 cm$^3$ of a 0.25 molar hexane solution of Mg(Bu)$_2$. The autoclave is then closed, brought to 70° C. and connected, by means of a flexible connection to an ethylene cylinder, equipped with a pressure reducer, placed on a balance. The autoclave is pressurized to 6.5 Bar keeping the pressure constant, by means of the reducer, for the whole duration of the test, reading the absorption of ethylene on the lance. The polymerization is carried out for 0.5 hours after the ethylene flow has been interrupted. The autoclave is ventilated, cooled and the contents discharged in methanol. The polymer is washed with methanol and dried under vacuum at 40° C. 20 g of polymer are recovered.

EXAMPLE 33

The polymerization of ethylene using a catalyst consisting of Y(toluene)(AlCl$_3$C$_4$H$_9$)$_3$ and Mg(Bu)$_2$ in hexane, is illustrated.

Carrying out all the operations described in example 32, 200 cm$^3$ of anhydrous hexane, 10 cm$^3$ of a 0.015 molar toluene solution of Y(toluene)(AlCl$_3$C$_4$H$_9$)$_3$ prepared according to example 16, Procedure 1, 10 cm$^3$ of a 0.25 molar hexane solution of Mg(Bu)$_2$, are charged into the autoclave in order. Polymerization is carried out at 70° C. for an hour. After washing and drying 22 g of polymer are recovered.

We claim:

1. Organometallic complexes comprising lanthanides, which can be represented with the general formula, $$\text{Me(Ar)(AlX}_3\text{R)}_3 \tag{I}$$

wherein:

Me represents a metal of the group IIIA, having atomic number 21, 39, or an atomic number of between 57 and 71, Ar represents benzene or a benzene substituted with from 1 to 3 alkyl groups containing from 1 to 10 carbon atoms, X is a halogen atom, whereas, R is a linear, cyclic or branched alkyl radical containing from 1 to 12 carbon atoms.

2. Organometallic complexes according to claim 1, characterized in that Me respectively represents an Yttrium atom (Y), a Neodymium (Nd) or Praseodymium (Pr) atom, a Gadolinium (Gd) atom and Ytterbium (Yb) atom.

3. Organometallic complexes according to claim 1, characterized in that X represents a chlorine or bromine atom.

4. Organometallic complexes according to claim 1, characterized in that Ar is a molecule of, toluene or tetramethylbenzene.

5. Organometallic complexes according to claim 1, characterized in that R is a methyl, propyl, isopropyl, n-butyl or ter-butyl group.

6. Process for the preparation of organometallic complexes comprising lanthanides, represented by the general formula, $$\text{Me(Ar)(AlX}_3\text{R)}_3 \tag{I}$$

comprising the steps of:

(a) forming a suspension of a complex of the general formula:

$$\text{Me (Ar)(AlX}_4\text{)}_3 \tag{II}$$

in a solvent, said solvent being aromatic, aliphatic, or cyclo-alyphatic, and maintaining the temperature at room temperature;

(b) adding a solution of a compound of formula:

$$\text{AlR}_3 \tag{III}$$

in same said solvent wherein:

Me represents a metal of group IIIA, having atomic number 21, 39, or an atomic number of between 57 and 71, Ar represents benzene or a benzene substituted with from 1 to 3 alkyl groups containing from 1 to 10 carbon atoms, X is a halogen atom, whereas, R is a linear, cyclic or branched alkyl radical containing from 1 to 12 carbon atoms, and in such a quanity that the molar ratio (III)/(II)=1.5, and reacting at room temperature until the complete dissolution of the suspended solid (II).

7. Process for the preparation of organometallic complexes according to claim 6, characterized in that the reaction solvent used is a hydrocarbon which belongs to the group comprising benzene, toluene, hexane, cyclohexane or their mixtures.

8. Process for the preparation of organometallic complexes according to claim 6, characterized in that the solution of compound (III) is added to the suspension of compound (II) maintained under stirring, with a time range of between 30 and 60 minutes.

9. Process for the preparation of organometallic complexes according to claim 6, characterized in that the reaction is carried out until the complete dissolution by reaction of the solid in the suspension, within a time range of between 120 and 150 minutes from the beginning of the reaction.

* * * * *